United States Patent [19]

Picard

[11] 4,431,409
[45] Feb. 14, 1984

[54] ORTHODONTIC APPARATUS

[76] Inventor: Peter J. Picard, 1804 San Miguel Dr., Walnut Creek, Calif. 94596

[21] Appl. No.: 339,499

[22] Filed: Jan. 15, 1982

[51] Int. Cl.³ .............................................. A61C 3/00
[52] U.S. Cl. ........................................ 433/2; 433/213
[58] Field of Search ............... 433/2, 3, 49, 50, 53, 433/72, 75, 20, 213

[56] References Cited

U.S. PATENT DOCUMENTS

| | | |
|---|---|---|
| 1,082,052 | 12/1913 | Strang . |
| 1,424,707 | 8/1922 | Adler . |
| 2,545,249 | 3/1951 | Ackerman ............................ 433/72 |
| 2,566,414 | 9/1951 | Henry ................................... 433/20 |
| 3,277,576 | 10/1966 | Kraft . |
| 3,439,421 | 4/1969 | Perkowski . |
| 3,949,478 | 4/1976 | Schinhammer . |
| 4,183,141 | 1/1980 | Dellinger et al. . |
| 4,300,883 | 11/1981 | Mier ..................................... 433/49 |

FOREIGN PATENT DOCUMENTS 371672  4/1932  United Kingdom ................. 433/49

Primary Examiner—John J. Wilson
Attorney, Agent, or Firm—Ernest M. Anderson

[57] ABSTRACT

This invention relates generally to orthodontic apparatus for applying an array of brackets to a cast matrix of teeth. The apparatus is particularly useful in the practice of a novel method invented by applicant which is also disclosed herein.

The apparatus essentially comprises a pair of first and second supports mounted relative to each other for rectilinear movement, a plurality of grippers for holding and supporting an arch wire in a plane substantially parallel with the direction of rectilinear movement, and means for adjustably mounting said grippers to adjust the spacing therebetween and position the grippers relative to said first and second supports, whereby a cast matrix of teeth can be positioned on said second support in juxtaposed relation to a plurality of brackets mounted on an arch wire supported by said grippers and moved simultaneously into and out of precise contact with the brackets.

1 Claim, 22 Drawing Figures

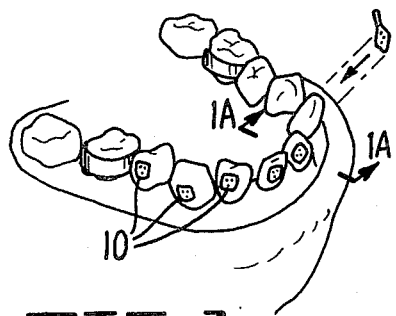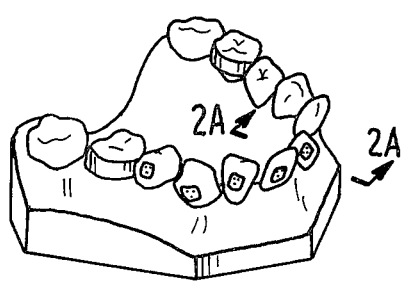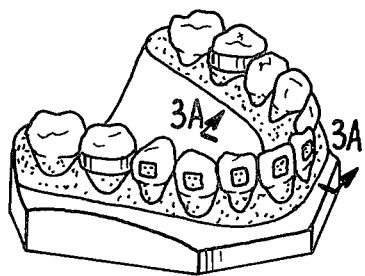
FIG.1. FIG.2. FIG.3.
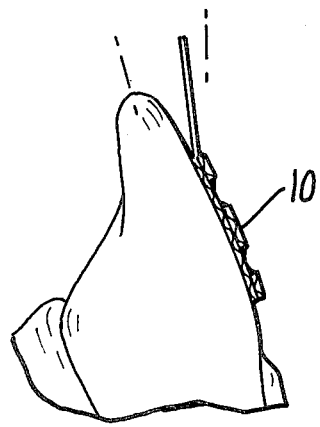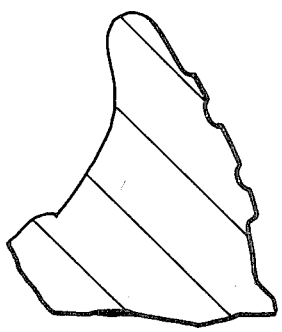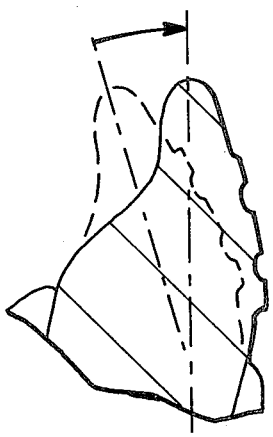
FIG.1A. FIG.2A. FIG.3A.
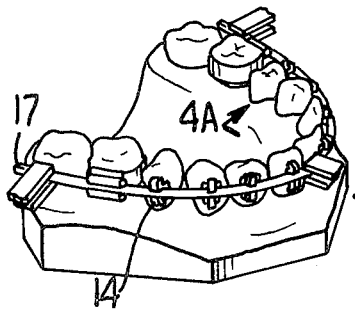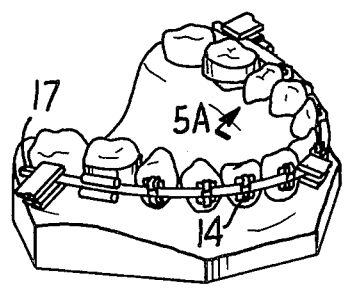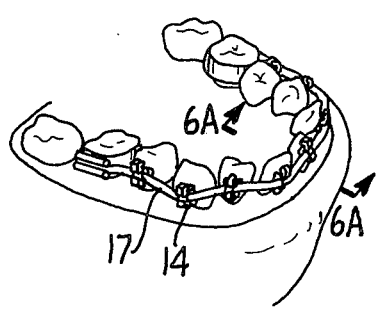
FIG.4. FIG.5. FIG.6.
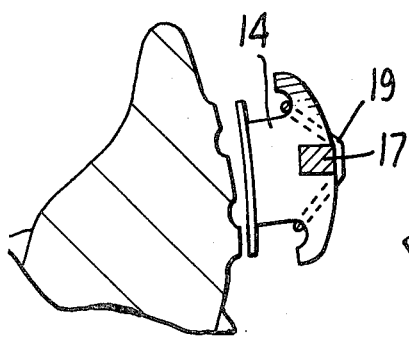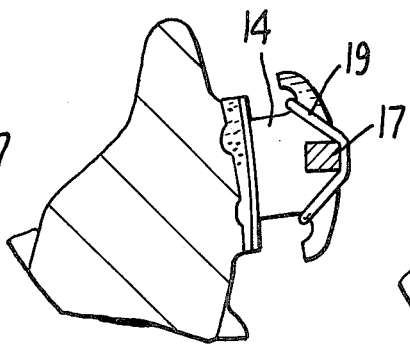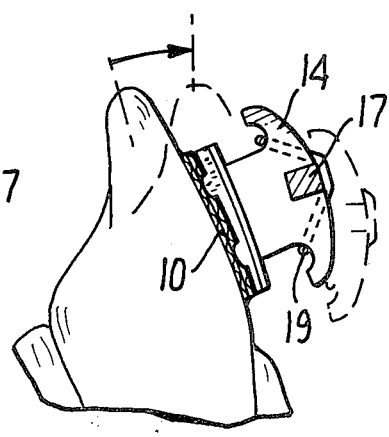
FIG.4A. FIG.5A. FIG.6A.

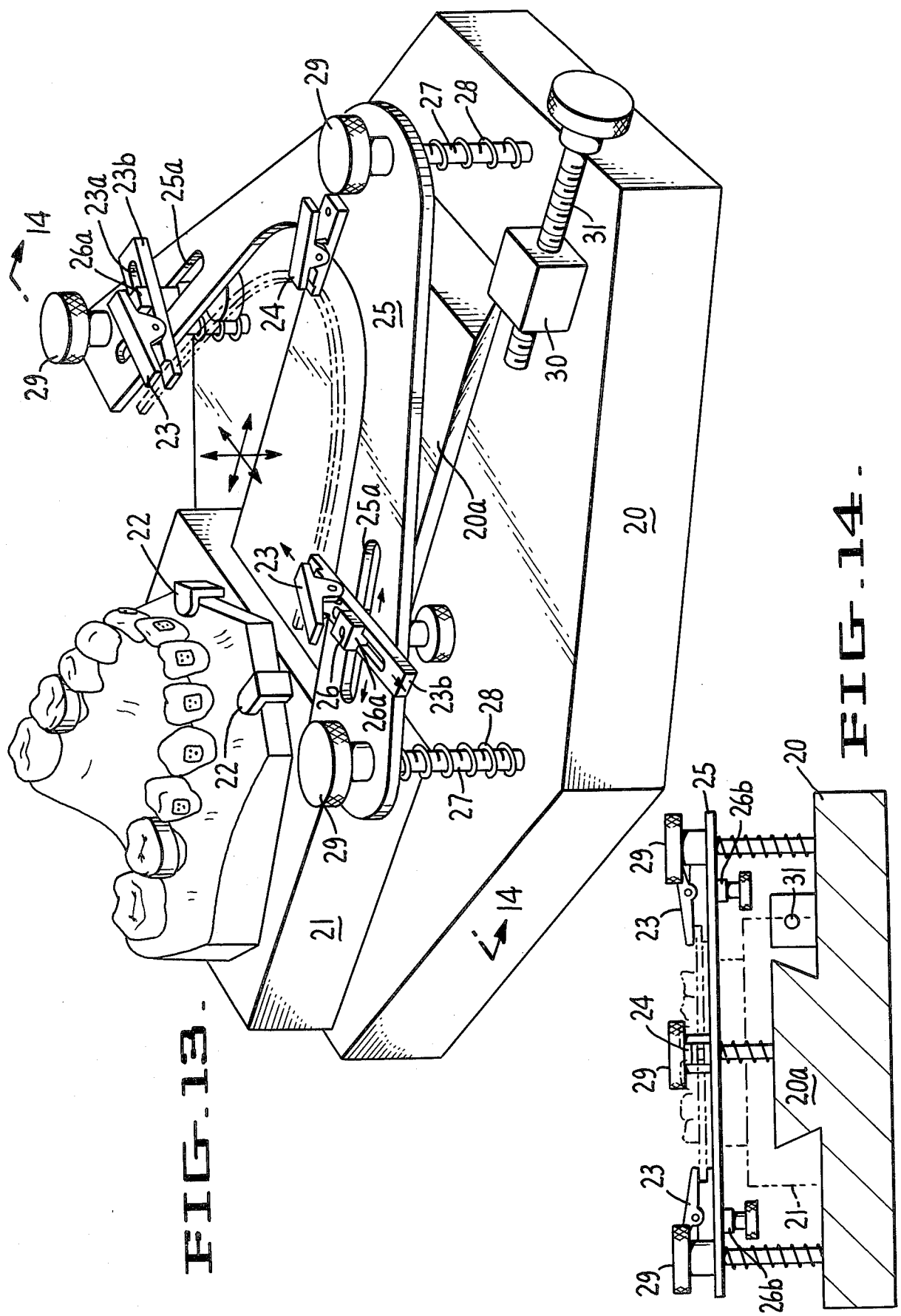

ORTHODONTIC APPARATUS

SUMMARY OF THE INVENTION

It is common practice to utilize an apparatus for fitting orthodontic brackets to teeth and utilizing positive dental arch models in effecting the proper adjustment and positioning of the brackets. Such an apparatus is disclosed in U.S. Pat. Nos. 3,949,478, 3,439,421 and 4,183,141.

A novel form of apparatus disclosed herein essentially provides a pair of supports that are mounted relative to each other for rectilinear movement. A plurality of grippers are provided for holding and supporting an arch wire on a plane substantially parallel with the direction of rectilinear movement, said grippers being adjustably mounted on one of the supports. The adjustable mounting of the grippers provides means for spacing the grippers relative to each other and to the pair of supports. A cast matrix of teeth can then be positioned on one support and moved rectilinearally relative to an arch wire with a plurality of brackets strung on the arch wire which is mounted on the other support. The cooperation and coaction of the two supports is an important tool for fitting each of the brackets to the cast matrix of teeth and in forming an interface layer or filler between each cast tooth and bracket.

Accordingly, one object of the present invention is to provide a novel apparatus for practicing a method whereby brackets may be applied to a cast matrix of teeth, while developing interface layers or fillers therebetween.

A further object of the invention is to provide an apparatus of the kind described that is capable of fully adjusting the position of brackets by means of an arch wire (upon which supported) relative to a cast matrix of teeth.

Other objects of this invention will become apparent in view of the following detailed description.

BRIEF DESCRIPTION OF THE DRAWINGS

In the drawings formally a part of this application and in which like parts are identified by like references throughout the same, FIGS. 1-6 illustrate six different steps or stages in the formation of interface layers of particular thickness and shape for the attachment of brackets to maloccluded teeth;

FIGS. 1a-6a illustrate vertical sections of tooth profiles representative of the stages of development in the formation of interface layers on the brackets, each figure being associated with the particular stage of development or step shown in the same numbered figure directly above;

FIGS. 13, 15 and 16 illustrate a preferred form of apparatus for attaching brackets to a cast matrix of teeth, each figure illustrating a different position of the apparatus; and FIG. 14 is a section of the apparatus taken on line 14—14 of FIG. 13.

DESCRIPTION OF THE PREFERRED EMBODIMENT

Figure 7:
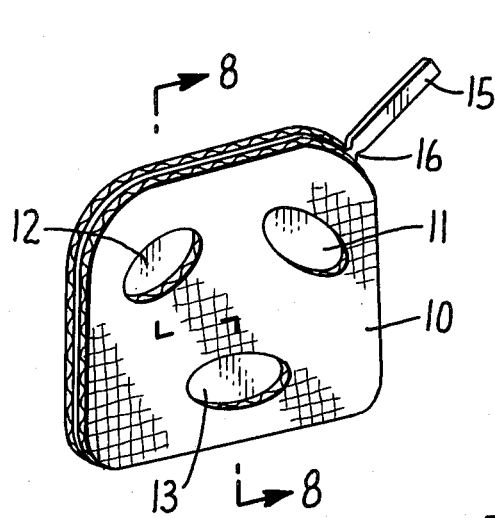
FIG. 7 illustrates a perspective view of a novel platelet that is utilized to form a locater surface on maloccluded teeth.
Figure 8:
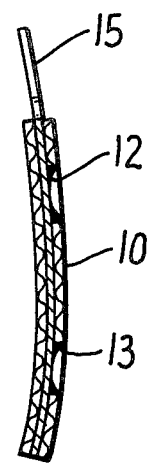
FIG. 8 is a vertical section of the platelet taken on lines 8—8 of FIG. 7.
Figure 9:
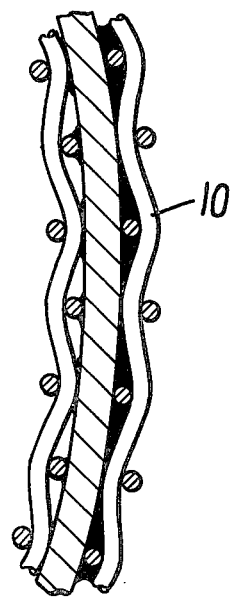
FIG. 9 is an enlarged detail and partial section of the platelet.

The method herein described relates to a new technical procedure that enables orthodontists to individualize tip, torque and in-out offset for each tooth and for each patient. The new procedure contemplates the use of conventional brackets, including the standard or the torqued-angulated varieties. It will be apparent that the new procedure eliminates many of the difficulties now encountered by the use of direct and indirect bonding. Although some of the steps of the process, and most of the material described and used, have been in use during various other dental procedures, novelty of the process resides in a combination of new steps and the use of newly designed parts which make the technique easier, more efficient and more comfortable for the patient. Most especially, the new technique, when utilized properly, finalizes the occlusion accurately.

Referring to FIGS. 1 and 1a in particular, the initial step of the process contemplates the formation of locater surfaces on all maloccluded teeth. This is preferably accomplished by means of attaching (or bonding) small wiremeshed platelets 10 to the maloccluded teeth in a patient's mouth. Each platelet 10 is slightly curved to conform with the tooth surface to which it is applied. The convex side of the platelet is formed with indentations that define smooth locater surfaces. A preferred embodiment of platelet comprises an impermeable center layer sandwiched between two wire mesh layers and a filler, said filler occupying the interstices of the wire mesh on the convex side to form a release surface. As shown, the platelets are intended for attachment to the buccal and labial surface. Notwithstanding, the procedure herein described is also applicable for placing platelets and brackets on the lingual surfaces of the teeth. In those instances, the platelets will be contoured to match the lingual surface of each tooth.

A preferred form of platelet utilizes three elongated and rounded indentations or depressions 11, 12 and 13. Sharp corners are to be avoided in forming the depressions since such corners may impair the release and the formation of a tooth casting as contemplated in the further procedure.

The arrangement of depressions provides locater surfaces which are to be matched by the surfaces of interface fillers formed on what may be considered standard brackets 14. Platelets 10 are preferably formed with essentially the same outline and contour as used for bases of conventional brackets. However, the size and contour of the platelets may vary between teeth just as do bases of brackets now conventionally employed.

In a preferred embodiment of platelet, each platelet is formed with a small handle 15, 3 mm. in length, extending at approximately 45° from their edge. This handle allows the platelet to be held during bonding and facilitates the attachment of platelets to teeth. A fracture line 16 may be formed between the handle and platelet to facilitate their removal.

After all platelets have been bonded to maloccluded teeth, handles are removed by fracturing and any objectionable fracture line is removed by polishing. An accurate impression of the dental arches with platelets bonded to teeth is now taken, and an orthodontic model is cast. Such a model or cast is shown in FIGS. 2 and 2a. Ordinarily, it is best to make two castings so that one can serve as a reference. In those instances it may be necessary to take two impressions. It may also be advisable to orient the model anatomically into an articulator instrument by means of the face bow transfer technique, a technique well known in this art.

At this stage of the process, one of the models is used for the construction of a so-called final set up or master matrix. This is accomplished by severing and repositioning the individual teeth on their plaster bases, thereby creating their exact final treatment position, and occlusion. FIGS. 3 and 3a illustrate such condition.

Referring now to FIGS. 4 and 4a, a plurality of brackets 14 having bases of substantially the same size and contour as the platelets are supported relative to the locater surfaces of the casting. Each bracket is formed with a rectangular slot 14a for receiving an arch wire 17. Unlike so-called straight wire brackets, the slots need not be torqued or angulated relative to the bracket base, and the brackets are secured to the locater surfaces formed on the cast surfaces with a cementitious or hardenable material that forms a rigid interface layer 18. This procedure may be carried out with the apparatus shown in FIGS. 13–16 as follows:

A rectangular arch wire 17 is formed around the dental arch of the master matrix or casting. The arch wire is formed without incorporating first, second or third order bends, and it has neither tip nor torque correction. The size of the rectangular arch wire must be such as to fill the bracket slots completely without allowing any play in any direction. In the horizontal plane of support, the arch wire should be oversized if anything to provide rigidity.

The individual brackets are next placed or strung onto the arch wire and positioned relative to the respective cast teeth of the matrix. The brackets may be held on the wire with an elastic ring 19 such as that sold under the name "Alastik". This attachment allows each bracket to be moved on the arch wire in a mesio-distal direction only.

Figure 10:
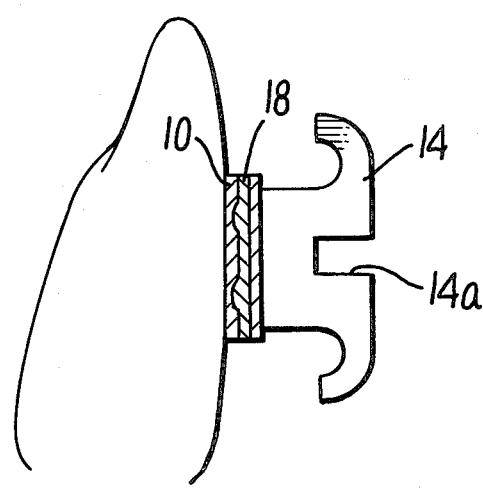
FIGS. 10, 11 and 12 illustrate three different conditions of bracket placement in the development of interface layers to accommodate the surface contour of a given tooth and to effect a specific correction of that tooth.
Figures 11, 12:
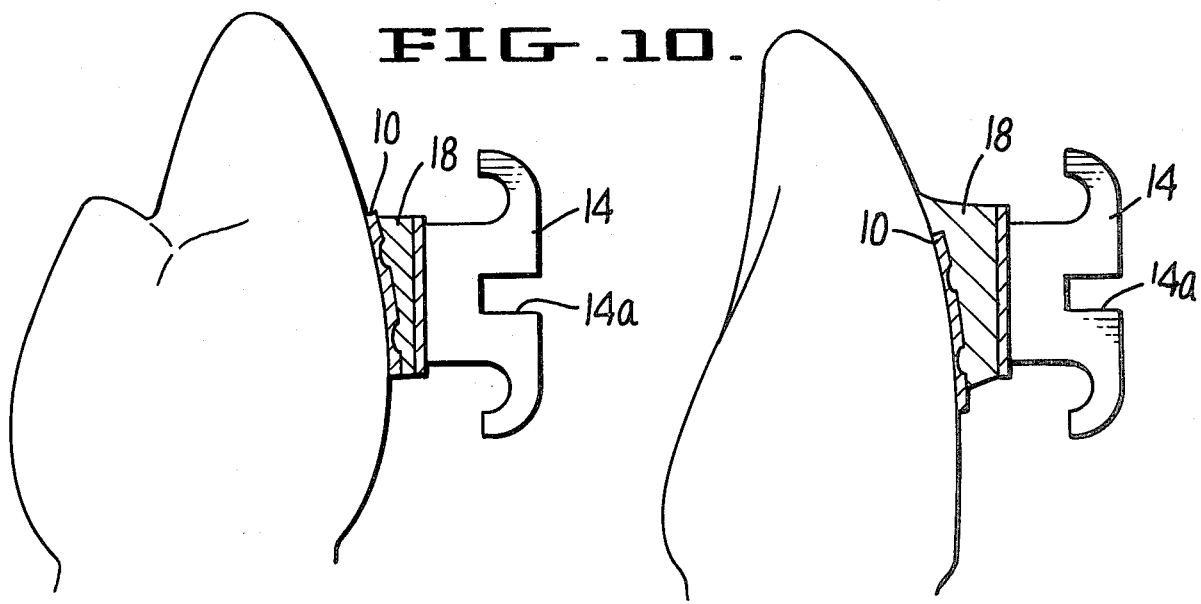

The brackets are now bonded onto the plaster replicas of platelets. In that process an interface filler is formed on each bracket, said filler surfaces taking on an imprint of the locater surfaces formed on the cast platelet surfaces. The interface fillers which are formed will ordinarily have varying degrees of thickness and contour and, as also shown in FIGS. 10, 11 and 12, it is not essential that the bracket base and platelet replicas match each other in total surface area. It is only necessary that the elevations formed on the surfaces of interface layers 18 match or fit the indentations of corresponding platelet replicas and platelets.

FIG. 12 illustrates the fact that a precise location of each bracket relative to the associated platelet is unnecessary. The interface layers may be formed as to overlap the platelets and the base of a bracket may be misaligned vertically (as shown) or both vertically and horizontally and even skew relative to the platelets. The indentations of the platelets and the matching raised surfaces formed on the interface layer serve as the means for locating each bracket in precise controlled relation to the tooth upon which it is to be mounted.

The molars, which usually are not bonded but receive bands, are handled in the following manner: Before taking the impressions for the set-up model, molars are banded and the occlusal of banded molars are covered with Kerr impression compound. Upon withdrawal of the impression, the compound remains seated in the impression material. The molar bands are now removed from the teeth and seated into the compound impression. The models are then poured up with bands seated in the impression material, and the set-up is made. After the set-up is completed, the plaster inside the bands, on the buccal surface, is carved out to provide a cavity for heat retention during soldering of bands to molar tubes. Thus, after all brackets have been bonded to the platelet replicas, molar tubes are threaded onto the arch wire and soldered to the molar bands.

The soldered connections, it should be noted, provide an angular set and alignment between bands and tubes and, therefore, perform a function similar to the interface layers or fillers 18.

Should it be desirable to have bonded tubes instead of tubes soldered to molar bands, then of course, placement of tubes would be handled in substantially the same manner as the brackets were bonded to platelet replicas. Bonded molar tubes would need either two platelets in tandem, or one specially fabricated molar platelet which would be longer in the mesiodistal direction and made to conform to the buccal anatomy of molars.

A preferred form of apparatus for attaching brackets to the cast matrix of teeth is illustrated in FIGS. 13–16. The apparatus comprises a pair of first and second supports, 20 and 21, mounted relative to each other for rectilinear movement. First support 20 comprises a platform having a central rail 20a, the cross-section of said rail have the shape of a dovetail. Second support 21 comprises a second platform formed with a dovetail groove 21a complimentary to the rail 20a. A pair of L shaped stops 22 are mounted to support 21 for positioning and securing the cast matrix of teeth.

The apparatus further comprises a plurality of grippers or clamps 23 and 24 for holding and supporting an arch wire in a plane substantially parallel to the direction of rectilinear movement. Means is also provided for adjustably mounting the grippers from support 20, such means providing an adjustment for laterally spacing the grippers as well as positioning the grippers vertically relative to supports 20 and 21. It will be evident, therefore, that by proper adjustment or location of the grippers, a cast matrix of teeth supported on second support or platform 21 can be positioned in juxtaposed relation to a plurality of brackets 14 mounted on an arch wire 17 supported by the grippers.

The adjustable mounting means comprises a support plate 25 supported from first support or platform 20 and having a recess into which a cast matrix of teeth can be moved. Grippers 23 are each mounted to plate 25 near the extremities thereof by means which allows each of them to be moved in any direction in a plane parallel to plate 25. For this purpose, a pair of slots 25a are formed in plate 25. A second pair of slots 23a are formed in a bar 23b which also forms one member of the gripper. A clamping bolt 26 projects through the slots 23a and 25a for securing each of the grippers 23 in a selected position for supporting the end portions of the arch wire. It will be apparent that both grippers 23 may be adjustably moved and positioned along both slot 25a and slot 23a.

A stop member 26a is mounted at the upper end of bolts 26, the lower end of each bolt being engaged by a threaded nut 26b which may be manually rotated.

Support plate 25 is also adjustably mounted from platform 20 by a plurality of posts 27 and helical springs 28. Posts 27 are secured to platform 20 and project through openings in plate 25, said plates resting upon and capturing helical springs 28. The upper ends of posts 27 are threaded and engage nuts 29. Rotation of the nuts forces plate 25 against the resilient bias of springs 28, positioning plate 25 relative to platforms 20 and 21.

An adjustable stop is also provided for setting the position of the matrix of teeth relative to an arch wire and allowing the matrix to be moved into and out of engagement with brackets supported upon an arch wire. The stop means comprises a block 30 mounted to platform 20 and a threaded member which extends through a threaded opening in said block.

Figure 15:
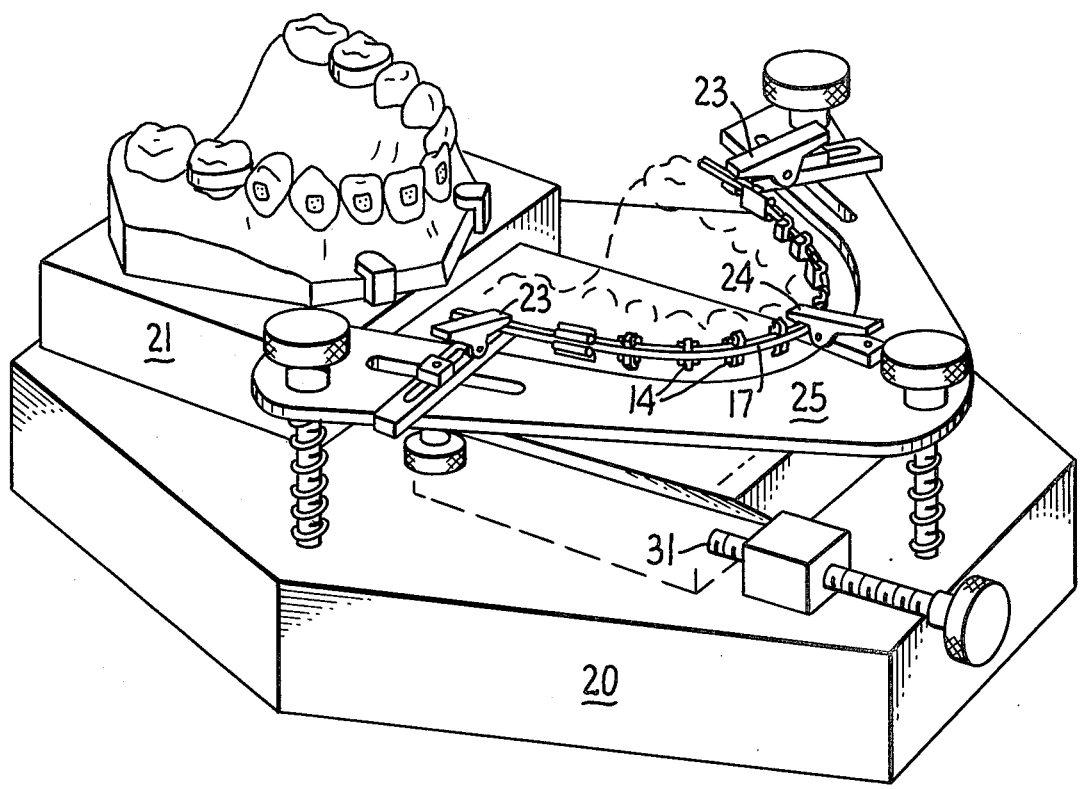
Figure 16:
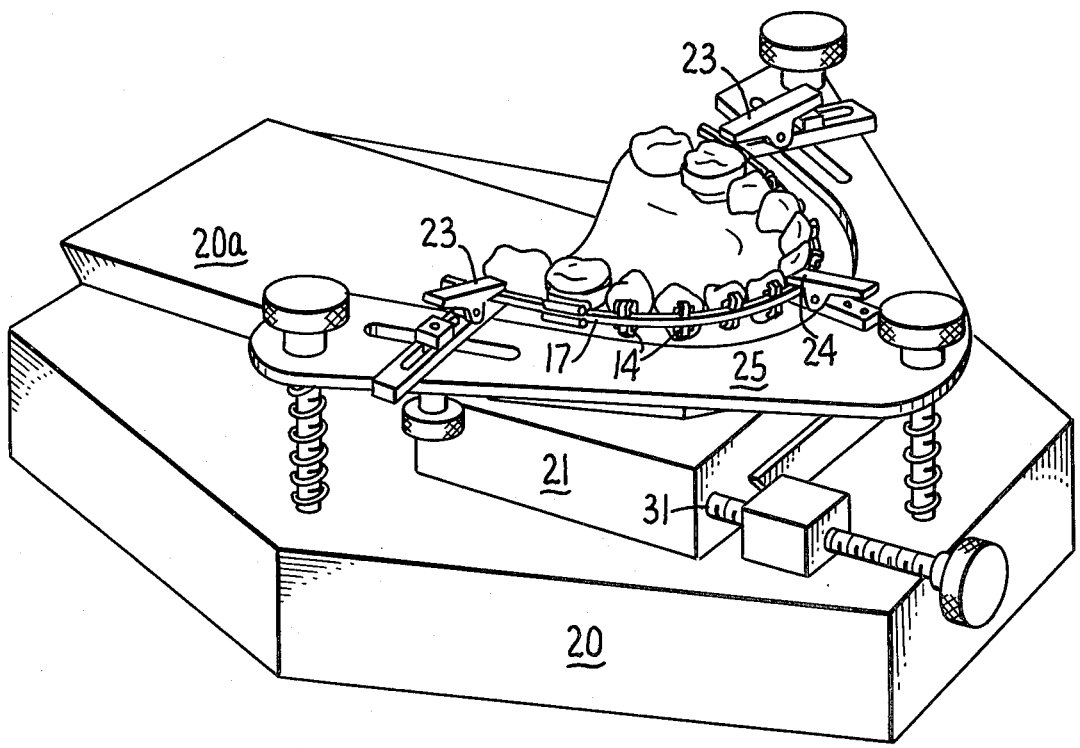

In operation of the apparatus, the matrix of cast teeth is set on platform 21 and positioned against stops 22 as shown in FIG. 13. An arch wire and brackets are then mounted to the grippers 23 and 24, as shown in FIG. 15. The arch wire is held by the grippers in a plane substantially parallel to the rectilinear direction in which platform 21 moves relative to platform 20. However, adjustments in location of grippers 23 and support plate 25 are utilized to precisely locate the brackets for selective mounting to the cast matrix of teeth. Such a position is shown in FIG. 16, all adjustments having been made as necessary to locate the brackets in their most desirable position relative to each tooth of the cast matrix. The stop means is thereupon adjusted to make contact with platform 21, the end of threaded member 31 making surface contact. This sets the position for cementing each bracket to its associated cast tooth and forming a filler interface on each bracket, the thickness, location and shape of the filler conforming to the cast teeth. The stop means allows platform 21 and the cast matrix of teeth to be backed away from the arch wire and brackets to permit filler cement to be applied to the brackets. After this has been done, the matrix is returned to a position of contact with the brackets by reference to the stop.

After the bonding material used to form the interface fillers has set, the Alastiks holding the arch wire to the bracket slots are removed and the wire is separated from the brackets by sliding the wire in the mesial direction. This allows the arch wire to be removed. Next the brackets are separated from the master matrix, the hardened bonding material adhering to each bracket base and showing its lingual surface imprint of the cast platelet. The bonding material is now cleaned of possible adhering plaster, and any material protruding beyond the edges of the bases is trimmed off.

The final step of the process involves locating and securing the brackets and attached interface fillers to the patient's teeth. The mouth and teeth are initially isolated and dried as during any bonding procedure. The brackets are then individually or in groups bonded to their respective platelets. Prior to final bonding, it is preferred to establish proper seating of the brackets onto their respective platelets, the surfaces of the interface fillers matching the imprint of the platelet. After proper fitting is assured, a small amount of bonding material is placed onto the platelet, and the associated bracket and interface filler is seated. Because of the matching surfaces between filler and platelet, the operator need not be concerned about proper bracket alignment nor drifting of the bracket as commonly experienced in previous direct bonding techniques.

The methods herein described provide a bracket mounting wherein all bracket torque, angulation and labial-lingual offsetting is provided by the formation of the interface filler. Moreover, correction of each tooth is individualized. To keep the interface thin, it is suggested that all brackets used for this technique should have a very low profile. Notwithstanding, the tip torque type of bracket can be used as well by keeping the interface filler to a minimum thickness.

Although a preferred embodiment of apparatus has been illustrated and described, various modifications and changes may be resorted to without departing from the spirit of the invention or the scope of the appended claims, and each of such modifications and changes is contemplated.

What is claimed is:

1. An orthodontic apparatus comprising, in combination:
   a cast matrix of teeth in which each cast tooth to be repositioned has a cast of a locating platelet rigidly attached thereto, and in which each of said cast teeth to be repositioned has been repositioned in said matrix to its desired position,
   a pair of first and second supports mounted relative to each other for rectilinear sliding movement relative to each other,
   a plurality of grippers mounted on said first support and supporting an arch wire in a plane substantially parallel with the direction of rectilinear movement, said arch wire carrying a plurality of brackets,
   means for positioning said cast matrix of teeth on said second support,
   means for adjustably mounting said grippers to adjust the spacing therebetween and to position the grippers along with said arch wire and brackets relative to said matrix of teeth, and
   interface filler means for each cast tooth with a locating platelet, said interface filler means rigidly bonding to each of said brackets and taking on an imprint of a cast locating platelet, whereby each of said brackets with an interface filler may be thereafter mounted in a patient's mouth directly on a corresponding locating platelet.

* * * * *